(12) United States Patent
Gloor et al.

(10) Patent No.: US 6,465,698 B2
(45) Date of Patent: Oct. 15, 2002

(54) CATALYTIC ISOMERIZATION OF Z-PENTOL TO E-PENTOL

(75) Inventors: Arnold Gloor, Basel; Hansjoerg Gruendler, Rheinfelden; Werner Simon, Riehen, all of (CH)

(73) Assignee: Roche Vitamins, Inc., Parsippany, NJ (US)

( * ) Notice: Subject to any disclaimer, the term of this patent is extended or adjusted under 35 U.S.C. 154(b) by 0 days.

(21) Appl. No.: 09/878,858

(22) Filed: Jun. 11, 2001

(65) Prior Publication Data

US 2002/0042547 A1 Apr. 11, 2002

(30) Foreign Application Priority Data

Jun. 30, 2000 (EP) .............................. 00113884

(51) Int. Cl.⁷ .............................. C07C 33/04

(52) U.S. Cl. ..................................... 568/873

(58) Field of Search ................................. 568/873, 840

(56) References Cited

PUBLICATIONS

Aase Strand and Synnøve Liaaen–Jensen, "Application of Diphenyl Diselenide as a New Catalyst for Photochemical Steroisomerization of Carotenoids," *Acta Chemica Scandinavica*, vol. 52, pp. 1263–1269 (1998).

Chatgilialoglu, et al., "(Z)–(E) Interconversion of Olefins by the Additon–Elimination Sequence of the $(TMS)_3Si$ Radical[1]," J. Org. Chem., vol. 60, pp. 3826–3831 (1995).

Peters, et al., "Competition between Isomerization and Addition in the Sonication of Vinyl Sulfones in the Presence of Bromotrichloromethane," J. prakt. Chem., vol. 337, pp. 363–367 (1995).

*Primary Examiner*—Samuel Barts
*Assistant Examiner*—Elvis O. Price
(74) *Attorney, Agent, or Firm*—Bryan Cave LLP

(57) ABSTRACT

A process for catalytically isomerizing Z-3-methylpent-2-en-4-yn-1-ol to E-3-methylpent-2-en-4-yn-1-ol is provided. This process includes contacting a stereoisomeric mixture containing Z-3-methylpent-2-en-4-yn-1-ol and E-3-methylpent-2-en-4-yn-1-ol with a source of bromine radicals in a two-phase reaction mixture having an aqueous phase and a stereoisomeric mixture phase, intermixing the reaction mixture, and heating the reaction mixture to a temperature from about –10° C. to about 100° C.

43 Claims, No Drawings

CATALYTIC ISOMERIZATION OF Z-PENTOL TO E-PENTOL

FIELD OF THE INVENTION

The present invention concerns a process for the catalytic isomerization of Z-3-methylpent-2-en-4-yn-1-ol to E-3-methylpent-2-en-4-yn-1-ol, hereinafter referred to for brevity as the isomerization of "Z-pentol" to "E-pentol."

BACKGROUND OF THE INVENTION

The known acid-catalyzed allylic rearrangement of 3-methylpent-1-en-4-yn-3-ol affords in thermodynamic equilibrium an isomeric mixture of Z- and E-pentol in the ratio Z-:E-pentol of about 85:15. These stereoisomers can if desired be separated from each other by physical means, e.g. by fractional distillation, to afford each stereoisomer in relatively good purity. The stereoisomer produced and isolated in the larger proportion, i.e. Z-pentol, is a useful intermediate, e.g. for the manufacture of vitamin A, and the stereoisomer produced and isolated in the smaller proportion, i.e. E-pentol, is also a useful intermediate, in this case e.g. for the manufacture of astaxanthin, zeaxanthin and further carotenoids. The situation may be schematically illustrated as follows, whereby the formulae are presented by conventional line representation:

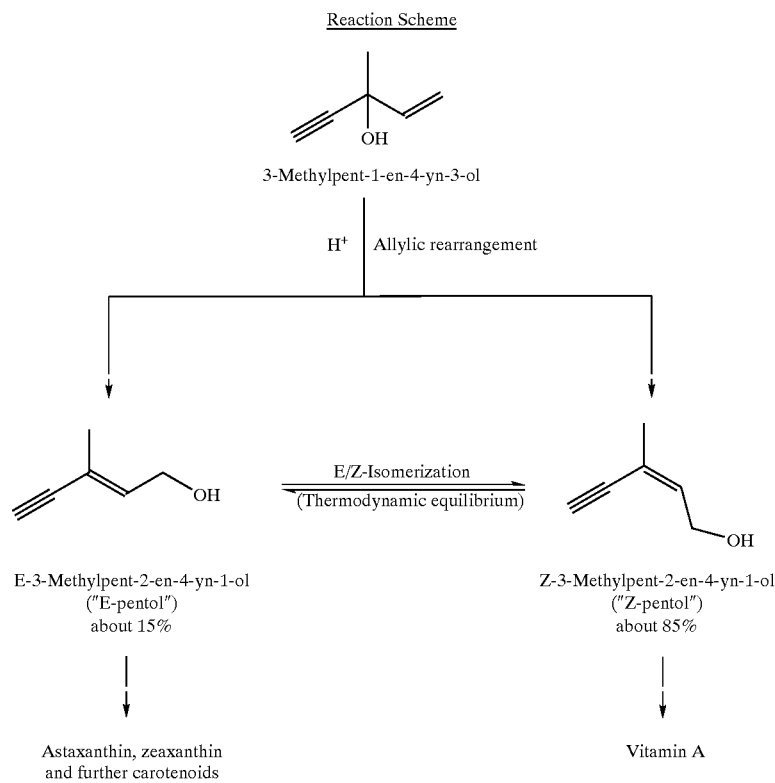

According to the relative requirement for one or the other stereoisomer depending on the relative amounts of the carotenoid and vitamin A end products to be produced therefrom, there exists an economical need to shift the above equilibrium of E- and Z-pentol from the thermodynamic one, and to influence the stereoisomeric ratio of these two useful intermediates. It is seldom economically feasible to separate the stereoisomers from a mixture in the thermodynamic equilibrium (about 85:15 Z-:E-pentol) as above. Indeed, since Z-pentol is the thermodynamically more stable pentol product, a shifting of the equilibrium in the direction Z-→E-entails an input of energy which would be justified if the relative requirement for astaxanthin, zeaxanthin and further carotenoids significantly exceeds about 15% of the total of both isomers. In this case, for example, there exists a need for a process for isomerizing a mixture of Z- and E-pentol, e.g. one in thermodynamic equilibrium with a Z-:E-ratio of about 85:15, to one with an increased proportion, i.e. higher than about 15%, of E-pentol.

SUMMARY OF THE INVENTION

This need has been surprisingly achieved by the catalytic isomerization process of the present invention which involves the use of bromine radicals (Br.) as the catalyst for isomerizing Z-pentol to E-pentol in a mixture of both these stereoisomers.

One embodiment of the invention is a process for catalytically isomerizing Z-3-methylpent-2-en-4-yn-1-ol to E-3-methylpent-2-en-4-yn-1-ol is provided. This process includes contacting a stereoisomeric mixture containing Z-3-methylpent-2-en-4-yn-1-ol and E-3-methylpent-2-en-4-yn-1-ol with a source of bromine radicals in a two-phase reaction mixture having an aqueous phase and a stereoisomeric mixture phase, intermixing the reaction mixture, and heating the reaction mixture to a temperature from about −10° C. to about 100° C.

DETAILED DESCRIPTION OF THE INVENTION

In principle any chemical system for generating the bromine radicals necessary for the performance of the catalytic isomerization process of the present invention may be utilized in the process, and each such chemical system gives rise to a particular embodiment of the process.

Common to all the chemical systems for generating bromine radicals is the actual source of bromine radicals, which is suitably an alkali metal or alkaline earth metal bromide, or ammonium bromide. As the alkali metal or alkaline earth metal bromide there comes into consideration particularly sodium or potassium bromide or, respectively, calcium or magnesium bromide. Preferably sodium bromide or potassium bromide is employed as the source of the bromine radicals.

The amount of such bromide salt employed relative to the amount of pentol starting material (mixture of Z- and E-pentols) is suitably about 0.2 mole to about 5 moles/mole, preferably about 0.2 mole to about 1 mole/mole, most preferably about 0.2 mole to about 0.5 mole/mole.

In one embodiment of the present invention, a salt of a heavy metal is used as the catalyst for promoting the generation of bromine radicals from the source thereof. Oxygen is generally used as an auxiliary agent for promoting the bromine radical generation. Examples of the heavy metals (cationic constituents) of these salts are titanium, vanadium, chromium, manganese, cobalt, nickel, zirconium, niobium, praseodymium, hafnium and lead. Examples of the anionic constituents of these salts are chloride, bromide, oxide, sulphate, oxychloride ($OCl_2^{4-}$) and acetate. Specific examples of such heavy metal salts are titanous chloride ($TiCl_3$), vanadium trichloride ($VCl_3$), vanadium dioxide ($V_2O_4$), vanadium pentoxide ($V_2O_5$), chromic chloride ($CrCl_3$), manganous bromide ($MnBr_2$), manganese dioxide ($MnO_2$), manganous sulphate ($MnSO_4$), manganous acetate ($Mn(OCOCH_3)_2$), manganic acetate ($Mn(OCOCH_3)_3$), cobaltous bromide ($CoBr_2$), nickelous bromide ($NiBr_2$), zirconic oxychloride ($ZrOCl_2$) niobium pentoxide ($Nb_2O_5$), praseodymium chloride ($PrCl_3$), praseodymium oxide ($Pr_6O_{11}$), hafnium tetrachloride ($HfCl_4$) and plumbous bromide ($PbBr_2$). A heavy metal bromide is preferably used as the catalyst. Independently of the nature of the anion, manganese, especially manganous ($Mn^{2+}$) salts, are preferably used as the catalysts.

The amount in moles of the heavy metal salt employed relative to the amount of pentol starting material (mixture of Z- and E-pentols) is suitably about 0.001 mole to about 0.5 mole/mole, preferably about 0.001 to about 0.3 mole/mole, most preferably about 0.01 to about 0.03 mole/mole.

As indicated above, oxygen is also generally used in the promotion of the bromine radical generation. As will be evident from the nature of the heavy metal salts, various oxidation potentials (levels) are represented by the metal ions in the salts, from as low as 2+, e.g. manganese(II) (manganous) in $MnBr_2$, $MnSO_4$ and $Mn(OCOCH_3)_2$, to as high as 4+, e.g manganese(IV) in $MnO_2$, or even 5+, e.g. vanadium(V) and niobium(V) in $V_2O_5$ and $Nb_2O_5$, respectively. The function of the oxygen, if used, is to raise the oxidation level of the heavy metal cations to render them effective in generating the bromine radicals from the bromide anions present. Thus a relatively low concentration of heavy metal cations with a high oxidation level suffices to generate the bromine radicals. For example, $Mn^{2+}$ ions can be elevated to $Mn^{3+}$ ions with oxygen, and a relatively small amount of such $Mn^{3+}$ ions enables the bromine radicals to be generated. Indeed, if heavy metal cations of a sufficiently high oxidation level are present at the outset, the presence of oxygen may be omitted. As a further example, $Mn^{2+}$ ions are not able to generate bromine radicals from the bromide in the absence of oxygen, but $Mn^{3+}$ ions can do this.

In those cases where oxygen is used as an auxiliary agent for the bromine radical generation, it can be used alone or in admixture with an inert gaseous component, e.g. with nitrogen in air. The oxygen gas or gas mixture, preferably containing at least 5 vol. % of oxygen, may be continuously passed through the two-phase reaction medium during the isomerization process. The rate of oxygen or oxygen mixture passage is about 5 l/h to about 200 l/h, preferably about 20 l/h to about 50 l/h. The technical means of oxygen passage is unimportant to the present process and may be achieved using conventional technical methodology, such as with a stirrer having jet outlets through which the oxygen is passed and released continuously into the stirred reaction medium. The oxygen gas or gas mixture can be used under pressure, suitably at a pressure up to a maximum of about 50 bar (5 MPa), which serves to accelerate the isomerization.

In the process of the present invention the mixture of pentol stereoisomers may form the pentol phase, or the stereoisomers may be dissolved in an essentially water-immiscible organic solvent. Such a solvent is suitably an alkane, e.g. pentane, hexane or heptane; an aromatic hydrocarbon, e.g. benzene or toluene; a chlorinated alkane, e.g. methylene chloride, chloroform or carbon tetrachloride; or an aliphatic ether, e.g. diethyl ether or diisopropyl ether. The aqueous phase serves to dissolve the alkali metal, alkaline earth metal or ammonium bromide, i.e. the source of the bromine radicals, and also the heavy metal salt. The aqueous phase may be an aqueous methanolic solution.

The catalytic isomerization process according to this first embodiment is effected in a pH range from about 0 to about 2.5. It has been established that on conducting the process at higher pH values, e.g. from about pH 2.5 to about pH 4.0, the yield of the desired E-pentol is increasingly reduced as the pH value is increased. The preferred pH range is from about 0.5 to about 1.

To adjust the pH value, the presence of a strong mineral acid, i.e. one with a pKa value of less than about 2, or of the organic acid, acetic acid, in the reaction medium is required. For this purpose there may suitably be used hydrochloric, hydrobromic, sulphuric, nitric or perchloric acid as the mineral acid, or, as mentioned above, acetic acid. The chosen acid is added in sufficient quantity, also if necessary during the initiated isomerization process, to bring or maintain the pH within the above range. If acetic acid is used, this is preferably approximately 50% aqueous acetic acid. Preferably hydrobromic acid is used as the strong mineral acid.

As mentioned above the catalytic isomerization process of the present invention is effected at temperatures from about −10° C. to about 100° C. If the first embodiment is used, the temperature range for both a batch and a continuous methodology is more suitably from about 0° C. to about 70° C., and in the case of a continuous methodology the temperature may even be suitably raised for short residence times of a few minutes to about 90° C. Preferably the temperature is from about 40° C. to about 60° C.

The isomerization process according to the first embodiment can be conducted using conventional procedural methodology. One suitable procedure involves heating a mixture of the bromide salt, the heavy metal salt and the acid required for pH adjustment in water to the desired reaction temperature under intensive mixing, e.g. through stirring, and then adding the mixture of pentol stereoisomers, as such or in solution in the essentially water-immiscible organic solvent, and also starting the oxygen passage. Intensive stirring is continued during the isomerization.

After completion of the isomerization process there generally results a two-phase mixture of which the aqueous and the organic phases can be separated by conventional means. The aqueous phase contains essentially the heavy metal salt catalyst, the bromide salt and the acid, and can be reused if desired for further isomerization reactions with a new Z- and E-pentol mixture. If necessary, additional bromide salt is added and/or the pH is adjusted by addition of more acid. The organic phase contains essentially as the dissolved material the Z/E-isomeric mixture of increased E-isomer content compared with that of the starting pentol mixture. The organic phase can be washed with water to neutrality by conventional means, and the pure E- and Z-isomers can be isolated therefrom for example by fractional distillation. The isolated E- and Z-pentols can then be used as desired, especially for the production of astaxanthin, zeaxanthin and further carotenoids and, respectively, for the production of vitamin A.

In a further embodiment of the present invention, there is used as the catalyst for promoting the generation of the bromine radicals a strong peroxide-type oxidizing agent. More particularly, such a catalyst is an alkali metal or alkaline earth metal peroxomonosulphate, peroxoborate, peroxodisulphate or peroxodiphosphate, or the system hydrogen peroxide/alkali metal or alkaline earth metal sulphate. In each case, the alkali metal is suitably sodium or potassium, and the alkaline earth metal is suitably calcium or magnesium. Examples of these catalysts include potassium peroxomonosulphate, sodium peroxoborate, sodium peroxodisulphate, potassium peroxodisulphate, potassium peroxodiphosphate and hydrogen peroxide/sodium sulphate. The catalyst is preferably a peroxodisulphate or the system hydrogen peroxide/alkali metal or alkaline earth metal sulphate, most preferably the latter catalyst system.

The amount in moles of strong peroxide-type oxidizing agent (catalyst) used for the isomerization reaction relative to the amount of pentol starting material is suitably about 0.01 to about 0.5 mole/mole, preferably about 0.015 to about 0.2 mole/mole. In the case of the hydrogen peroxide/sulphate catalyst system the hydrogen peroxide is conveniently used in aqueous solution, preferably at concentration of about 30%, and the amount of sulphate salt employed is conveniently about 0.1 to about 50 mole % of the molar amount of pentol starting material.

In contrast to the first embodiment described above, the present embodiment does not require oxygen as an auxiliary agent for promoting the generation of the bromine radicals. Indeed, this embodiment can be effected in an inert atmosphere, e.g. nitrogen or argon.

In the present embodiment the isomerization process is conveniently carried out in a two-phase medium in which the aqueous phase contains essentially the dissolved alkali metal, alkaline earth metal or ammonium bromide, i.e. the source of the bromine radicals, and optionally also added acid for any necessary pH adjustment. The organic phase is formed from the mixture of pentol stereoisomers, which may optionally be dissolved in an organic solvent. The organic solvent may be a chlorinated alkane, e.g. methylene chloride, chloroform or carbon tetrachloride; a lower, especially $C_{1-6}$-, alkanol, e.g. methanol, ethanol, isopropanol, n-butanol or tert. butanol; an aliphatic ketone, e.g. isobutyl methyl ketone; an aliphatic ester, e.g. ethyl acetate; acetonitrile; an organic carbonate, e.g. dimethyl carbonate; an alicyclic hydrocarbon, e.g. methylcyclohexane; or an aromatic hydrocarbon, e.g. toluene. The use of an organic solvent in the reaction medium appears to reduce this tendency of the pentol stereoisomers to decompose, and is also of advantage by facilitating the isolation of the product after the reaction.

Regardless of the use or not of an organic solvent to dissolve the mixture of pentol stereoisomers, the volume of water per mole of such pentol stereoisomer mixture is maintained at about 50 ml to about 800 ml of water/mole of pentol stereoisomer mixture, preferably about 50 ml to about 200 ml of water/mole of pentol stereoisomer mixture. If a low volume of water is used, i.e. about 50–100 ml, the temperature at which the isomerization reaction is conducted is suitably somewhat higher than if volumes above about 100 ml are used in order to compensate for the lower heat capacity of the reaction mixture.

The catalytic isomerization process according to this embodiment, and in contrast to the first embodiment, is less influenced by the pH of the reaction medium, and indeed can generally be effected in the broad pH range of about 0 to about 10. Accordingly, the addition of acid to the medium for adjustment of the pH is usually unnecessary. The preferred pH range is, however, from about 0 to about 7. By conducting the isomerization reaction in the neutral pH range, i.e. around pH 7, any partial decomposition of the pentol stereoisomers, which occurs to some extent in the acid pH range (less than pH 7), is considerably reduced. If pH adjustment is effected, the same kind of acid may be added to the reaction medium as set forth above for the previous embodiment.

The catalytic isomerization process of this embodiment for both a batch and a continuous methodology is suitably effected at temperatures from about −10° C. to about 70° C. In the case of a continuous methodology the temperature may even be raised for short residence times of a few minutes to about 100° C., whereby the tendency of the pentol stereoisomers to decompose at such higher temperatures must be observed by not prolonging unnecessarily the heating in the upper temperature range. The catalytic isomerization process is preferably effected at temperatures from about 40° C. to about 60° C.

The isomerization process according to this embodiment may also be conducted using conventional procedural methodology. An especially suitable methodology includes heating the two-phase medium consisting of the mixture of pentol stereoisomers, water, the bromide salt and any acid required for pH adjustment to the desired reaction temperature under gasification with an inert gas, such as nitrogen or argon, and under intensive mixing, e.g. through stirring, and then adding the catalyst as a crystalline solid or in aqueous solution. In the case of using the hydrogen peroxide/alkali metal or alkaline earth metal sulphate system as the catalyst, the above especially suitable methodology differs in that the sulphate is included in the two-phase medium for heating under gasification and intensive mixing to the desired reaction temperature. Then the hydrogen peroxide in aqueous solution is added. In all cases, the reaction mixture is suitably mixed further, e.g. by stirring, and if necessary, the pH adjusted periodically, until it has been established that the isomerization process has proceeded to a constant isomerization equilibrium or a substantially constant equilibrium. Thereafter, the mixture is suitably cooled, preferably to room temperature or thereabouts, and the isolation of the product effected.

After completion of the isomerization process according to this further embodiment there results a two-phase mixture with, in certain cases, a solid residue consisting of the insoluble salts, such as various sulphates, hydrogen sulphates etc. Any solid constituents can be readily removed, e.g by filtration. The remaining two-phase liquid medium containing the Z/E-isomeric mixture of pentols with increased E-isomer content in the organic phase and an aqueous phase containing the remaining dissolved salts are then treated essentially as described above in connection with the final isolation procedure of the first embodiment to afford the isolated E- and Z-pentols. In this case, too, the aqueous phase containing dissolved salts, or the salts isolated therefrom, can be reused if desired for further isomerization reactions with a new Z- and E-pentol mixture.

Regardless of the embodiment employed, the length of time required to achieve isomerization equilibrium depends on the particular reaction conditions employed, and can amount to a few minutes to several hours. As an example, in certain instances of the isomerization process being conducted at about 85° C. using the two-phase solvent system water and methylene chloride, the isomerization equilibrium is rapidly achieved, i.e. within about 2 minutes. In any event, such reaction conditions as the concentration of the bromide salt and the employed amount of catalyst exert a strong influence on the reaction duration.

The following examples are provided to further illustrate methods of preparation of the compositions of the present invention, as well as certain physical properties and uses thereof. These examples are illustrative only and are not intended to limit the scope of the invention in any way.

EXAMPLES

Example 1

149.55 g of potassium bromide, 5.85 g of manganous acetate tetrahydrate, 250 ml of water and 200 ml of glacial acetic acid were introduced successively into a reactor and the mixture was then stirred and warmed to 50° C. Air was led through the resulting stirred solution at a rate of 20 l/h, and 108.54 g of (mainly) Z-3-methylpent-2-en-4-yn-1-ol (98.7% of the Z-isomer and 1.0% of the E-isomer according to gas chromatography (GC)) were added dropwise over 10 minutes.

After a reaction duration of 1 hour the mixture was cooled down to room temperature, and with portionwise addition of 500 ml of water and 500 ml of methylene chloride, extracted into the organic phase in each case. The combined organic phases were concentrated at 30° C. under reduced pressure, yielding 176.16 g of a dark brown liquid. According to GC, the liquid contained 47.4% of Z-3-methylpent-2-en-4-yn-1-ol and 5.9% of the E-isomer. This corresponds to a yield of 8.7% of E-3-methylpent-2-en-4-yn-1-ol from the initially available Z-isomer.

Example 2

Low oxygen air (5 vol. % $O_2$ and 95 vol. % $N_2$) was introduced at a rate of 20 l/h through the sintered glass filter of a double-walled reactor fitted with a sintered glass base, followed by 99.7 g of potassium bromide, 2.72 g of manganous sulphate monohydrate and 300 ml of 0.25N sulphuric acid. The mixture was stirred and warmed to 70° C. Then the rate of introduction of the low oxygen air was increased to 50 l/h, and 72.36 g of (mainly) Z-3-methylpent-2-en-4-yn-1-ol (composition as in Example 1) were introduced over 10 minutes. After a stirring period of 1 hour at 70° C. the introduction of low oxygen air was stopped and the resulting two-phase reaction mixture was released from the reactor through the sintered glass filter via the exit conduit at the base.

The dark brown organic phase of the released reaction mixture was separated from the aqueous phase and washed with water, and the aqueous phase was washed with 30 ml of diisopropyl ether. A GC analysis of the combined organic and diisopropyl ether phases indicated a yield 11.8% of E-3-methylpent-2-en-4-yn-1-ol from the initially available Z-isomer.

Example 3

450 ml of water, 149.55 g of potassium bromide and 6.99 g of manganous bromide tetrahydrate were introduced successively into a double-walled reactor. The mixture was stirred and heated to 50° C. After adjustment of the pH to 1.0 with 6.0 ml of 30% hydrobromic acid, air was passed through the mixture at a rate of 20 l/h and 109.11 g of (mainly) Z-3-methylpent-2-en-4-yn-1-ol (98.6% of the Z-isomer and 0.6% of the E-isomer according to GC) were added portionwise over 10 minutes. After stirring and air passage at 50° C. for 1 hour, the mixture was cooled to 25° C. and the two phases separated from each other.

The organic phase was washed with 45 ml of water, and the aqueous phase extracted with 45 ml of diisopropyl ether. A GC analysis of the combined organic and diisopropyl ether phases indicated a yield of 13.5% of E-3-methylpent-2-en-4-yn-1-ol from the initially available Z-isomer.

Example 4

149.55 g of potassium bromide, 2.28 g of manganese dioxide and 450 ml of 0.25N sulphuric acid were introduced successively into a double-walled reactor and the mixture was then stirred and warmed to 50° C. 4.5 ml of 62% hydrobromic acid were added to the mixture for fully dissolving the manganese dioxide, whereupon the pH of the solution was 0.8, and within 15 minutes thereafter 121.77 g of (mainly) Z-3-methylpent-2-en-4-yn-1-ol (containing water; 87.8% of the Z-isomer and 1.1% of the E-isomer according to GC) were added portionwise. After stirring at 50° C. for 1 hour, the mixture was cooled to 25° C. and the two phases separated from each other.

The dark brown organic phase was washed with 45 ml of water and the aqueous phase was extracted with 45 ml of diisopropyl ether. A GC analysis of the combined organic and diisopropyl ether phases indicated a yield of 6.0% of E-3-methylpent-2-en-4-yn-1-ol from the initially available Z-isomer.

Example 5

Under an atmosphere of argon, 196 g of (mainly) Z-3-methylpent-2-en-4-yn-1-ol (about 98% of the Z-isomer and about 1% of the E-isomer according to GC), 244.3 g of potassium bromide and 703.5 g of 0.25N sulphuric acid were introduced successively into a double-walled reactor. The mixture was then stirred and warmed to 50° C. Then, 50 g of manganic acetate dihydrate were added as rapidly as possible, causing the pH of the reaction mixture to rise from 0.5 to 3.7. Addition of 50% sulphuric acid adjusted the pH to 0.9, at which pH value the reaction was continued for the next 3 hours. After this reaction period and subsequent cooling to room temperature, a GC analysis was effected which indicated that the yield of E-3-methylpent-2-en-4-yn-1-ol, taken from both liquid phases of the mixture, from the initially available Z-isomer, amounted to 12.9%.

Example 6

Under an atmosphere of argon, 303.75 g of potassium bromide, 435 ml of 0.135N hydrobromic acid, 109.11 g of (mainly) Z-3-methylpent-2-en-4-yn-1-ol (composition as in Example 3) and 10 ml of water were introduced successively into a double-walled reactor. The mixture was then stirred and warmed to 50° C. Then, 16.2 g of potassium peroxodisulphate were added in one portion, and the reaction mixture was stirred for a further 15 minutes at 50° C., after which it was cooled to 20° C.

The solid salts which had precipitated out of the mixture on standing at 20° C. were filtered off under reduced pressure and the two liquid phases separated from each other. The organic phase was washed with 45 ml of water, and the aqueous phase together with the precipitated salts were extracted with 50 ml of diisopropyl ether. A GC analysis of the combined organic and diisopropyl ether phases indicated a yield of 13.5% of E-3-methylpent-2-en-4-yn-1-ol from the initially available Z-isomer.

Example 7

Under an atmosphere of argon, 147.96 of potassium bromide, 424 ml of 0.135N hydrobromic acid, 106.71 g of (mainly) Z-3-methylpent-2-en-4-yn-1-ol (97,6% of the Z-isomer and 1.1% of the E-isomer according to GC) and 10 ml of water were introduced successively into a double-walled reactor. The mixture was then stirred and warmed to 50° C. Then, 24.77 g of potassium peroxodiphosphate were added in one portion, which raised the pH of the reaction mixture from 0.6 to 5.4. Using 30% hydrobromic acid the pH was adjusted to 1.0. With the use of a pH-stat, the pH value 1.0 was maintained during the whole 4 hours duration of the isomerization reaction. After this reaction period, the mixture was cooled to 25° C.

The two liquid phases were then separated from each other. The organic phase was washed with 45 ml of water, and the aqueous phase was extracted with 45 ml of diisopropyl ether. A GC analysis of the combined organic and diisopropyl ether phases indicated a yield of 7.0% of E-3-methylpent-2-en-4-yn-1-ol from the initially available Z-isomer.

Example 8

Under an atmosphere of argon 151.87 g of potassium bromide, 370 ml of 0.159N hydrobromic acid, 109.11 g of (mainly) Z-3-methylpent-2-en-4-yn-1-ol (composition as in Example 3) and 10 ml of water were introduced successively into a double-walled reactor. The mixture was then stirred and warmed to 50° C. Using a dosage pump, a solution of 19.01 g of potassium peroxomonosulphate (47%) in 65 ml of water was added portionwise within 30 minutes to the reaction mixture at 50° C. There followed a further 3.5 hours reaction period, after which the mixture was cooled to 25° C.

The two liquid phases were separated from each other. The organic phase was washed with 45 ml of water, and the aqueous phase with 45 ml of diisopropyl ether. A GC analysis of the combined organic and diisopropyl ether phases indicated a yield of 3.6% of E-3-methylpent-2-en-4-yn-1-ol from the initially available Z-isomer.

Example 9

Under an atmosphere of argon 29.21 g of sodium bromide, 7.57 g of sodium sulphate, 50 ml of water and 96.66 g of (mainly) Z-3-methylpent-2-en-4-yn-1-ol (98.5% of the Z-isomer and 0.9% of the E-isomer according to GC) were introduced successively into a sulphonation flask, and the mixture was warmed to 50° C. with stirring. 10.4 ml of 30% hydrogen peroxide were then added dropwise within 15 minutes and the reaction mixture was stirred at 50° C. for 4 hours. During this reaction time the pH of the mixture rose from 5.3 to 6.1.

Then the mixture was cooled to 20° C. and the precipitated salts removed by filtration. A GC analysis of the two liquid phases indicated a yield of 14.3% of E-3-methylpent-2-en-4-yn-1-ol from the initially available Z-isomer.

Example 10

Under an atmosphere of argon 262.63 g of sodium bromide, 250 ml of water and 109.53 g of (mainly) Z-3-methylpent-2-en-4-yn-1-ol (composition as in Example 7) were introduced successively into a double-walled reactor and the mixture was then stirred and warmed to 50° C. A solution of 14.12 g of sodium peroxodisulphate in 200 ml of water, previously exposed to argon, was added to the mixture in the reactor with intensive stirring, causing a change in pH from 5.65 to 2.25. After a further 30 minutes stirring at 50° C., the isomerization had been completed. A GC analysis of both the liquid phases indicated a yield of 14.3% of E-3-methylpent-2-en-4-yn-1-ol from the initially available Z-isomer.

Examples 11–24

Using the same procedures set forth in Examples 1–4 various heavy metal salts (promoters of bromine radical generation) were used, and the resulting yields of Z-→E-isomer conversion quantified. Standard reaction conditions were employed in these experiments as follows:

For 14.42 g (0.15 mole) of 3-methylpent-2-en-4-yn-1-ol (98.5% of the Z-isomer and 0.5% of the E-isomer according to GC) there were employed, per mole of the starting material, 0.021 mole of heavy metal salt and 1.117 mole of potassium bromide. Completing the reaction mixture were in each case 60 ml of 0.135 N hydrobromic acid. The rate of air passage was 20 l/h. At a reaction temperature of about 50° C., the isomerization was allowed to proceed for 2–3 hours.

The nature of the promoter and the yield in each example are presented in the Table below:

TABLE

| Example | Promoter | Yield (%) |
|---|---|---|
| 11 | $MnBr_2$ | 13.1 |
| 12 | $V_2O_4$ | 10.7 |
| 13 | $VCl_3$ | 10.7 |
| 14 | $Pr_6O_{11}$ | 7.5 |
| 15 | $PrCl_3$ | 7.2 |
| 16 | $CrCl_3$ | 6.3 |
| 17 | $NiBr_2$ | 5.5 |
| 18 | $V_2O_5$ | 5.4 |
| 19 | $ZrOCl_2$ | 5.0 |
| 20 | $CoBr_2$ | 4.9 |
| 21 | $TiCl_3$ | 4.5 |
| 22 | $PbBr_2$ | 2.8 |
| 23 | $HfCl_4$ | 2.7 |
| 24 | $Nb_2O_5$ | 2.1 |

The invention being thus described, it will be obvious that the same may be varied in many ways. Such variations are not to be regarded as a departure from the spirit and scope of the invention and all such modifications are intended to be included within the scope of the following claims.

What is claimed is:

1. A process for catalytically isomerizing Z-3-methylpent-2-en-4-yn-1-ol to E-3-methylpent-2-en-4-yn-1-ol comprising:

(a) contacting a stereoisomeric mixture containing Z-3-methylpent-2-en-4-yn-1-ol and E-3-methylpent-2-en-4-yn-1-ol with a source of bromine radicals in a two-phase reaction mixture having an aqueous phase and a stereoisomeric mixture phase;

(b) intermixing the reaction mixture; and (c) heating the reaction mixture to a temperature from about −10° C. to about 100° C.

2. A process according to claim 1 wherein the stereoisomeric mixture is present in a water-immiscible organic solvent.

3. A process according to claim 1 wherein the source of the bromine radicals is an alkali metal or alkaline earth metal bromide, or an ammonium bromide.

4. A process according to claim 1 wherein the source of the bromine radicals is sodium bromide or potassium bromide.

5. A process according to claim 3 wherein the amount of the bromide relative to the amount of the stereoisomeric mixture is about 0.2 to about 5 moles/mole.

6. A process according to claim 5 wherein amount of the bromide relative to the amount of the stereoisomeric mixture is about 0.2 to about 1 mole/mole.

7. A process according to claim 6 wherein amount of the bromide relative to the amount of the stereoisomeric mixture is about 0.2 to about 0.5 mole/mole.

8. A process according to claim 1 further comprising promoting the generation of the bromine radicals from the source thereof using a salt of a heavy metal as the catalyst.

9. A process according to claim 8 further comprising promoting the bromine radical generation by adding oxygen to the reaction mixture as an auxiliary agent.

10. A process according to claim 9 further comprising determining whether the oxidation level of the heavy metal cation is sufficient to generate bromine radicals from the bromide anions, and if the level of heavy metal cations is determined to be sufficient to generate the bromine radicals, omitting the oxygen addition step.

11. A process according to claim 8 wherein the heavy metal of the heavy metal salt is selected from the group consisting of titanium, vanadium, chromium, manganese, cobalt, nickel, zirconium, niobium, praseodymium, hafnium and lead, and the anionic constituent of the salt is selected from chloride, bromide, oxide, sulphate, oxychloride and acetate.

12. A process according to claim 11 wherein the salt of the heavy metal salt is selected from the group consisting of titanous chloride ($TiCl_3$), vanadium trichloride ($VCl_3$), vanadium dioxide ($V_2O_4$), vanadium pentoxide ($V_2O_5$), chromic chloride ($CrCl_3$), manganous bromide ($MnBr_2$), manganese dioxide ($MnO_2$), manganous sulphate ($MnSO_4$), manganous acetate ($Mn(OCOCH_3)_2$), manganic acetate ($Mn(OCOCH_3)_3$), cobaltous bromide ($CoBr_2$), nickelous bromide ($NiBr_2$), zirconic oxychloride ($ZrOCl_2$), niobium pentoxide ($Nb_2O_5$), praseodymium chloride ($PrCl_3$), praseodymium oxide ($Pr_6O_{11}$), hafnium tetrachloride ($HfCl_4$), and plumbous bromide ($PbBr_2$).

13. A process according to claim 8 wherein the amount of the heavy metal salt relative to the amount of the stereoisomeric mixture is about 0.001 to about 0.5 mole/mole.

14. A process according to claim 13 wherein the amount the heavy metal salt relative to the amount of the stereoisomeric mixture is about 0.001 to about 0.3 mole/mole.

15. A process according to claim 14 wherein the amount the heavy metal salt relative to the amount of the stereoisomeric mixture is about 0.01 to about 0.03 mole/mole.

16. A process according to claim 8 further comprising dissolving the stereoisomeric mixture in a water-immiscible organic solvent selected from the group consisting of an alkane, an aromatic hydrocarbon, a chlorinated alkane, an aliphatic ether, and mixtures thereof.

17. A process according claim 16 wherein the alkane is selected from the group consisting of pentane, hexane, heptane, and mixtures thereof.

18. A process according claim 16 wherein the aromatic hydrocarbon is selected from the group consisting of benzene, toluene, and mixtures thereof.

19. A process according claim 16 wherein the chlorinated alkane is selected from the group consisting of methylene chloride, chloroform, carbon tetrachloride, and mixtures thereof.

20. A process according to claim 16 wherein the aliphatic ether is selected from the group consisting of diethyl ether, diisopropyl ether, and mixtures thereof.

21. A process according to claim 8 further comprising carrying out the reaction at a pH from about 0 to about 2.5.

22. A process according to claim 21 wherein the pH is from about 0.5 to about 1.

23. A process according to claim 1 further comprising promoting the generation of the bromine radicals from the source thereof using a strong peroxide-type oxidizing agent as the catalyst.

24. A process according to claim 23 wherein the strong peroxide-type oxidizing agent is an alkali metal or alkaline earth metal peroxomosulphate, peroxoborate, peroxodisulphate or peroxodiphosphate.

25. A process according to claim 23 wherein the strong peroxide-type oxidizing agent is a hydrogen peroxide/alkali metal or alkaline earth metal sulphate system.

26. A process according to claim 25 wherein the alkali metal is sodium or potassium and the alkaline earth metal is calcium or magnesium.

27. A process according to claim 23 wherein the strong peroxide-type oxidizing agent is selected from the group consisting of potassium peroxomonosulphate, sodium peroxoborate, sodium peroxodisulphate, potassium peroxodisulphate, potassium peroxodiphosphate, and hydrogen peroxide/sodium sulphate.

28. A process according to claim 23 wherein the amount of strong peroxide-type oxidizing agent used relative to the amount of the stereoisomeric mixture is about 0.01 to about 0.5 mole/mole.

29. A process according to claim 28 wherein the amount of the strong peroxide-type oxidizing agent used relative to the amount of the stereoisomeric mixture is about 0.015 to about 0.2 mole/mole.

30. A process according to claim 25 wherein the hydrogen peroxide is present as an aqueous solution at a concentration of about 30%, and the amount of sulphate salt present in the system is about 0.1 to about 50 mole % of the molar amount of the stereoisomeric mixture.

31. A process according to claim 25 wherein the stereoisomeric mixture is dissolved in an organic solvent selected from the group consisting of a chlorinated alkane, a lower alkanol, an aliphatic ketone, an aliphatic ester, acetonitrile, an organic carbonate, an alicyclic hydrocarbon, an aromatic hydrocarbon, and mixtures thereof.

32. A process according to claim 31 wherein the chlorinated alkane is selected from the group consisting of methylene chloride, chloroform, carbon tetrachloride, and mixtures thereof.

33. A process according to claim 31 wherein the lower alkanol is a $C_{1-6}$-alkanol.

34. A process according to claim 33 wherein the $C_{1-6}$-alkanol is selected from the group consisting of methanol, ethanol, isopropanol, n-butanol, tert, butanol, and mixtures thereof.

35. A process according to claim 31 wherein the aliphatic ketone is isobutyl methyl ketone.

36. A process according to claim 31 wherein the aliphatic ester is ethyl acetate.

37. A process according to claim 31 wherein the organic carbonate is dimethyl carbonate.

38. A process according to claim 31 wherein the alicyclic hydrocarbon is methyl-cyclohexane.

39. A process according to claim 31 wherein the aromatic hydrocarbon is toluene.

40. A process according to claim 23 wherein the volume of water per mole of the stereoisomeric mixture is about 50 ml to about 800 ml per mole of the stereoisomeric mixture.

41. A process according to claim 40 wherein the volume of water per mole of the stereoisomeric mixture is about 50 ml to about 200 ml per mole of the stereoisomeric mixture.

42. A process according to claim 23 further comprising
(a) heating the two-phase medium consisting of the stereoisomeric mixture, water, a bromide salt and any acid required for pH adjustment under gasification with an inert gas;
(b) mixing the two phase medium; and
(c) adding the catalyst as a crystalline solid or as an aqueous solution to the two phase medium, wherein when the catalyst is the hydrogen peroxide/alkali metal or alkaline earth metal sulphate system, the sulphate of the catalyst system is added to the two-phase medium of step (a), and the hydrogen peroxide of the catalyst system in aqueous solution, is then added after step (b).

43. A process according to claim 42 wherein the inert gas is nitrogen or argon.

* * * * *

UNITED STATES PATENT AND TRADEMARK OFFICE
CERTIFICATE OF CORRECTION

PATENT NO.    : 6,465,698 B2
DATED         : October 15, 2002
INVENTOR(S)   : Arnold Gloor et al.

It is certified that error appears in the above-identified patent and that said Letters Patent is hereby corrected as shown below:

<u>Title page,</u>
Item [75], Inventors, the city of residence of "Arnold Gloor" is incorrect. Therefore, please change "Basel" to -- Basle --;
Item [56], References Cited, please insert:
-- FOREIGN PATENT DOCUMENTS
EP 0 621 254 A2
FR 2 703 044
Derwent English language abstract of FR 2 703 044 --;

<u>Column 11,</u>
Lines 17 and 20, after "wherein" please insert -- the --;
Lines 57 and 60, after "amount" please insert -- of --;

<u>Column 12,</u>
Lines 1, 4 and 7, after "according" please insert -- to --;
Line 25, please change "peroxomosulphate" to -- peroxomonosulphate --;
Line 66, please change "tert, butanol" to -- tert.butanol --.

Signed and Sealed this

Second Day of September, 2003

JAMES E. ROGAN
*Director of the United States Patent and Trademark Office*